(12) United States Patent
Tarran et al.

(10) Patent No.: US 11,634,420 B2
(45) Date of Patent: Apr. 25, 2023

(54) COMPOUNDS FOR USE IN ORGANIC ELECTRONIC DEVICES

(71) Applicant: Sumitomo Chemical Company Limited, Tokyo (JP)

(72) Inventors: William Tarran, Godmanchester (GB); James Lee, Godmanchester (GB); Nazrul Islam, Cambourne (GB)

(73) Assignee: Sumitomo Chemical Company Limited, Tokyo (JP)

( * ) Notice: Subject to any disclaimer, the term of this patent is extended or adjusted under 35 U.S.C. 154(b) by 515 days.

(21) Appl. No.: 16/622,270

(22) PCT Filed: Jun. 14, 2018

(86) PCT No.: PCT/GB2018/051634
§ 371 (c)(1),
(2) Date: Dec. 12, 2019

(87) PCT Pub. No.: WO2018/229491
PCT Pub. Date: Dec. 20, 2018

(65) Prior Publication Data
US 2020/0181145 A1 Jun. 11, 2020

(30) Foreign Application Priority Data
Jun. 15, 2017 (GB) ..................... 1709565

(51) Int. Cl.
*C07D 471/16* (2006.01)
*H01L 51/00* (2006.01)
(Continued)

(52) U.S. Cl.
CPC ......... *C07D 471/16* (2013.01); *C07D 487/16* (2013.01); *H01L 51/0051* (2013.01); *H01L 51/0072* (2013.01); *H01L 51/5092* (2013.01)

(58) Field of Classification Search
None
See application file for complete search history.

(56) References Cited

U.S. PATENT DOCUMENTS

| | | |
|---|---|---|
| 2010/0041880 A1 | 2/2010 | Becker et al. |
| 2010/0187515 A1 | 7/2010 | Limmert et al. |

FOREIGN PATENT DOCUMENTS

EP  1 837 926 A1  9/2007

OTHER PUBLICATIONS

International Preliminary Report on Patentability for Interational Application No. PCT/GB2018/051634 dated Dec. 26, 2019.
(Continued)

*Primary Examiner* — Jay Yang
(74) *Attorney, Agent, or Firm* — Wolf, Greenfield & Sacks, P.C.

(57) ABSTRACT

A compound of formula (I): (Formula (I)) wherein $Ar^1$, $Ar^2$ and $Ar^3$ independently in each occurrence is a $C_{6-20}$ aryl group or a 5-20 membered heteroaryl group which is unsubstituted or substituted with one or more substituents; $X^1$, $X^2$ and $X^3$ in each occurrence is independently a direct bond or a group of formula —$C(R^1)_2$— wherein $R^1$ in each occurrence is independently H or a substituent. The compound of formula (I) may be used to form an n-dopant for doping an organic semiconductor. A film formed by such n-doping may be used in an organic electronic device, for example an electron injection layer of an organic light-emitting device.

18 Claims, 5 Drawing Sheets (I)

(51) Int. Cl.
  *C07D 487/16* (2006.01)
  *H01L 51/50* (2006.01)

(56) References Cited

OTHER PUBLICATIONS

GB 1709565.4, Apr. 5, 2018, Combined Search and Examination Report.
PCT/GB2018/051634, Aug. 8, 2018, International Search Report and Written Opinion.
Combined Search and Examination Report for Application No. GB 1709565.4 dated Apr. 5, 2018.
International Search Report and Written Opinion for International Application No. PCT/GB2018/051634 dated Aug. 8, 2018.
Banerji et al., Heterocycles in Organic Synthesis. Part 3. Reversible Dearomatisation of Azoles: Formation of Triazabenzophenanthrenes. Journal of the Chemical Society, Perkin Transactions I: Organic and Bio-Organic Chemistry. 1977;10:1162-6. ISSN: 0300-922X.
Banerji et al., Reactions of amidines with diphenylamine-2,2'-dicarbonyl chloride. Heterocycles. 1983;20(4):617-21. ISSN: 0385-5414.
Cass et al., Dearomatisation by Use of Multifunctional Reagents: Reaction of Bis-(1-chloroformyl)-diphenylamine with Imidazole Derivatives. Journal of the Chemical Society, Chemical Communications. 1976;2:48. ISSN: 0022-4936.
Harlow et al., 4b,9a,13b-Triazadibenzo[a,e]acephenanthrylene-9,14-dione. Acta Crystallographica, Section B: Structural Crystallography and Crystal Chemistry. 1976;B32(5):1606-8. ISSN: 0567-7408.
Lunn et al., Formation of Triazabenzacephenanthrylium Salts. Their Solvolysis and Borohydride Reduction. Journal of Organic Chemistry. 1972;37(4):607-11. ISSN: 0022-3263.

COMPOUNDS FOR USE IN ORGANIC ELECTRONIC DEVICES

RELATED APPLICATIONS

This Application is a national stage filing under 35 U.S.C. § 371 of international PCT application PCT/GB2018/051634, filed Jun. 14, 2018, which claims priority to United Kingdom patent application no. GB 1709565.4, filed Jun. 15, 2017, each of which is incorporated herein by reference in its entirety.

FIELD OF THE INVENTION

The invention relates to compounds for use in organic electronic devices, in particular compounds for use as an n-dopant precursor.

BACKGROUND OF THE INVENTION

Electronic devices containing active organic materials include organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An organic light-emitting device has a substrate carrying an anode, a cathode and an organic light-emitting layer containing a light-emitting material between the anode and cathode.

In operation, holes are injected into the device through the anode and electrons are injected through the cathode. Holes in the highest occupied molecular orbital (HOMO) and electrons in the lowest unoccupied molecular orbital (LUMO) of the light-emitting material combine to form an exciton that releases its energy as light.

Cathodes include a single layer of metal such as aluminium, a bilayer of calcium and aluminium as disclosed in WO 98/10621; and a bilayer of a layer of an alkali or alkali earth compound and a layer of aluminium as disclosed in L. S. Hung, C. W. Tang, and M. G. Mason, Appl. Phys. Lett. 70, 152 (1997).

An electron-transporting or electron-injecting layer may be provided between the cathode and the light-emitting layer.

Bao et al, "Use of a 1H-Benzoimidazole Derivative as an n-Type Dopant and To Enable Air-Stable Solution-Processed n-Channel Organic Thin-Film Transistors" J. Am. Chem. Soc. 2010, 132, 8852-8853 discloses doping of [6,6]-phenyl $C_{61}$ butyric acid methyl ester (PCBM) by mixing (4-(1,3-dimethyl-2,3-dihydro-1H-benzoimidazol-2-yl)phenyl)dimethylamine (N-DMBI) with PCBM and activating the N-DMBI by heating.

US 2014/070178 discloses an OLED having a cathode disposed on a substrate and an electron-transporting layer formed by thermal treatment of an electron-transporting material and N-DMBI. It is disclosed that a radical formed on thermal treatment of N-DMBI may be an n-dopant.

US 2010/0187515 discloses n-dopant precursors for doping organic semiconductive materials.

US 2007/0252140 discloses heterocyclic radicals and diradicals used as n-dopants.

It is an object of the invention to provide an n-dopant precursor having increased stability.

It is a further object of the invention to provide a solution processable n-dopant having increased solution stability.

SUMMARY OF THE INVENTION

In a first aspect the invention provides a compound of formula (I):

(I)

wherein $Ar^1$, $Ar^2$ and $Ar^3$ independently in each occurrence is a $C_{6-20}$ aryl group or a 5-20 membered heteroaryl group which is unsubstituted or substituted with one or more substituents; and $X^1$, $X^2$ and $X^3$ in each occurrence is independently a direct bond or a group of formula —$C(R^1)_2$— wherein $R^1$ in each occurrence is independently H or a substituent.

A compound of formula (I) may be used as a precursor of an n-dopant for doping an organic semiconductor.

Accordingly, in a second aspect, the invention provides a composition comprising an organic semiconductor and a compound according the first aspect.

The present inventors have found that compounds of formula (I) may show stability in solution.

Accordingly, in a third aspect the invention provides a compound or a composition according to the first or second aspects and at least one solvent.

In a fourth aspect the invention provides a charge-transfer salt comprising an organic semiconductor doped by a dopant formed from a compound according to the first aspect.

In a fifth aspect the invention provides a method of forming a charge-transfer salt comprising the step of activating a composition according to the second aspect.

In a sixth aspect the invention provides an organic electronic device comprising a layer comprising a charge-transfer salt according to the fourth aspect.

In a seventh aspect the invention provides a method of forming an organic electronic device according to the sixth aspect, the method comprising the step of depositing the compound according to the first aspect from a polar solvent.

DESCRIPTION OF THE DRAWINGS

The invention will now be described in more detail with reference to the drawings in which:

FIG. 4 shows photoluminescence spectra of an organic semiconductor/n-dopant precursor composition according to

DETAILED DESCRIPTION OF THE INVENTION

The compounds of formula (I) as described herein may be used to form an n-dopant for n-doping of an organic semiconductor. Without wishing to be bound by any theory, it is believed that compounds of formula (I) may form n-dopants by cleavage of a C—H bond to form a radical capable of transferring an electron to the organic semiconductor.

Formula (I) is:

(I)

wherein $Ar^1$, $Ar^2$ and $Ar^3$ independently in each occurrence is a $C_{6-20}$ aryl group or a 5-20 membered heteroaryl group which is unsubstituted or substituted with one or more substituents; and $X^1$, $X^2$ and $X^3$ in each occurrence is independently a direct bond or a group of formula —$C(R^1)_2$— wherein $R^1$ in each occurrence is independently H or a substituent.

$R^1$ is preferably H or a $C_{1-20}$ alkyl group, more preferably H.

Preferably, at least one of $X^1$, $X^2$ and $X^3$ is a direct bond and at least one of $X^1$, $X^2$ and $X^3$ is a group of formula —$C(R^1)_2$—.

Preferably, $X^1$ is a direct bond.

Preferably, $X^2$ and $X^3$ are each a group of formula —$C(R^1)_2$—.

Preferably, $Ar^1$, $Ar^2$ and $Ar^3$ are each independently a $C_{6-20}$ aryl group, more preferably phenyl.

Each of $Ar^1$, $Ar^2$ and $Ar^3$ may be unsubstituted or substituted with one or more substituents.

In some embodiments, each of $Ar^1$, $Ar^2$ and $Ar^3$ is unsubstituted.

In some embodiments at least one, optionally two of or each of $Ar^1$, $Ar^2$ and $Ar^3$ is substituted with at least one group $R^2$ wherein $R^2$ is a substituent. Each of $Ar^1$, $Ar^2$ and $Ar^3$ substituted with at least one substituent is optionally substituted with 1, 2, 3 or 4 substituents, preferably one substituent.

Optionally, only one of $Ar^1$, $Ar^2$ and $Ar^3$ is substituted.

Optionally, $Ar^1$ is substituted with a substituent and $Ar^2$ and $Ar^3$ are unsubstituted.

Where present, each $R^2$ is independently a non-ionic substituent or an ionic substituent.

Non-ionic substituents are optionally selected from the group consisting of $C_{1-20}$ alkyl wherein one or more non-adjacent, non-terminal C atoms may be replaced with O, S, $NR^3$, $PR^3$, $Si(R^3)_2$, C=O, C(=O)O, C(=O)$NR^3$, OC(=O)O, $NR^3C(=O)O$, or $NR^3C(=O)NR^3$, and wherein one or more H atoms may be replaced with F, wherein $R^3$ independently in each occurrence is a $C_{1-20}$ hydrocarbyl group.

By "non-terminal C atom" of an alkyl group as used herein is meant a C atom of an alkyl group other than the methyl group of an n-alkyl chain or the methyl groups of a branched alkyl chain.

An ionic substituent $R^2$ is preferably selected from substituents of formula (III):

-(Sp$^1$)p-(A)q    (III)

wherein $Sp^1$ is a spacer group; A is an anion or cation; p is 0 or 1; q is 1 if p is 0; and q is at least 1, preferably 1, if p is 1, the compound further comprising one or more counterions B to balance the charge of the one or more anions or cations A.

Optionally, $Sp^1$ is selected from:

$C_{1-10}$ alkylene wherein one or more non-adjacent C atoms may be replace with O, S, C=O, COO or phenylene; and arylene or heteroarylene, preferably phenylene, that may be unsubstituted or substituted with one or more $C_{1-20}$ alkyl groups wherein one or more non-adjacent C atoms of the $C_{1-20}$ alkyl groups may be replaced with O, S, C=O or COO.

"$C_{1-10}$ alkylene" as used herein means a divalent carbon atom or divalent alkyl chain.

Optionally, arylene or heteroarylene groups of $Sp^1$ are selected from phenylene and 5 or 6 membered heteroarylene groups. Substituents of arylene or heteroarylene groups of $Sp^1$ are optionally selected from $C_{1-20}$ alkyl, optionally $C_{1-12}$ alkyl wherein one or more non-adjacent C atoms may be replaced with O, S, C=O or COO, preferably O.

A of formula (III) and B may have the same valency, with a counterion B balancing the charge of each A of formula (III).

Anion or cation A may be monovalent or polyvalent.

Preferably, A and B are each monovalent.

In another embodiment, the compound of formula (I) may comprise a plurality of anions or cations A, preferably monovalent anions or cations A, wherein the charge of two or more anions or cations A is balanced by a single, polyvalent counterion B. Optionally, the compound of formula (I) comprises one or more di- or trivalent cations B.

Exemplary anions A may be selected from, without limitation, sulfonate and —COO⁻. A preferred anion A is —COO⁻.

Exemplary cations A may be selected from organic or inorganic cations including, without limitation —$N(R^{11})_3^+$; —$P(R^{11})_3^+$; —$S(R^{11})_2^+$; or a heteroaromatic cation, optionally a heteroaromatic cation comprising or consisting of C and N atoms optionally pyridinium or imidazolium, wherein $R^{11}$ in each occurrence is H or $C_{1-12}$ hydrocarbyl, optionally $C_{1-12}$ alkyl. A preferred cation A is —$NR^{11}_3^+$.

Cation B is optionally a metal cation, optionally Li⁺, Na⁺, K⁺, Cs⁺, preferably Cs⁺, or an organic cation, optionally $N(R^{11})_4^+$ such as tetraalkylammonium, or a heteroaromatic cation optionally ethylmethyl imidazolium or pyridinium. The size of the cation may affect the dopant strength of the n-dopant. Preferably, the cation is an organic cation or a metal cation from the third or higher periods of the Periodic Table, preferably fourth or higher periods, more preferably fifth or higher periods of the Periodic Table.

Anion B is optionally halide, optionally F⁻, Cl⁻, Br⁻ or I⁻; hydroxide; a borate, optionally $BF_4^-$; a phosphate, optionally $PF_6^-$; a phosphinate; a phosphonate; an imide, optionally TFSI; or a sulfonate group, optionally mesylate, tosylate or sulfonate.

A hydrocarbyl group as described herein is optionally selected from $C_{1-20}$ alkyl, unsubstituted phenyl and phenyl substituted with one or more $C_{1-12}$ alkyl groups.

Exemplary compounds of formula (I) are:

Organic Semiconductor

The organic semiconductor may be a polymeric or non-polymeric material. Optionally, the organic semiconductor is a polymer, more preferably a conjugated polymer.

By "non-polymeric material" as used herein is meant non-polydisperse compounds, including, without limitation, non-polydisperse oligomeric materials comprising 2-10 repeat units.

The organic semiconductor may comprise a polar double or triple bond, optionally a bond selected from a C=N (imino) group, a nitrile group, a C=S group, an oxime group or a C=O group, optionally a keto, ester or carbonate group. Preferably, these polar double- or triple-bond groups are conjugated to a conjugated polymer backbone. These polar double- or triple-bond groups may be provided as substituents of a conjugated repeat unit or may be part of a conjugated repeat unit, for example fluorenone.

The organic semiconductor may be a polymer comprising electron-deficient repeat units.

The organic semiconductor may comprise benzothiadiazole repeat units, optionally repeat units of formula:

wherein $R^{10}$ in each occurrence is a substituent, optionally a substituent selected from alkyl, optionally $C_{1-20}$ alkyl, wherein one or more non-adjacent, non-terminal C atoms may be replaced with optionally substituted aryl or heteroaryl, O, S, C=O or —COO—, and one or more H atoms may be replaced with F.

A repeat unit comprising benzothiadiazole may have formula:

wherein $R^{10}$ is as described above with reference to benzothiadiazole.

The organic semiconductor may be a polymer comprising an arylene repeat unit substituted with one or more electron-withdrawing groups. An exemplary electron-withdrawing group is cyano.

Arylene repeat units include, without limitation, fluorene, phenylene, naphthalene, anthracene, indenofluorene, phenanthrene and dihydrophenanthrene repeat units, each of which may be substituted with one or more electron-withdrawing groups and optionally substituted with one or more further substituents. Exemplary further substituents, if present, may be selected from $C_{1-40}$ hydrocarbyl, for example $C_{1-20}$ alkyl, unsubstituted phenyl or phenyl substituted with one or more $C_{1-12}$ alkyl groups.

A polymer comprising an electron-deficient arylene repeat unit or a benzothiadiazole repeat unit may be a copolymer comprising one or more co-repeat units. The co-repeat units may be selected from arylene co-repeat units that are not substituted with an electron-withdrawing group and are optionally unsubstituted or substituted with one or more substituents selected from $C_{1-40}$ hydrocarbyl groups and ionic groups. Ionic substituents of a co-repeat unit may have formula (III) as described with reference to compounds of formula (I).

Polymers as described anywhere herein may have a polystyrene-equivalent number-average molecular weight (Mn) measured by gel permeation chromatography in the range of about $1\times10^3$ to $1\times10^8$, and preferably $1\times10^3$ to $5\times10^6$. The polystyrene-equivalent weight-average molecular weight (Mw) of polymers described anywhere herein may be $1\times10^3$ to $1\times10^8$, and preferably $1\times10^4$ to $1\times10^7$.

Polymers as described anywhere herein are suitably amorphous polymers.

The charge transfer complex may be formed from a mixture of the organic semiconductor material and a separate compound of formula (I), or the compound of formula (I) may be covalently bound to the organic semiconductor, in which case the organic semiconductor may be a polymer comprising a repeat unit substituted with the compound of formula (I).

Activation

The compound of formula (I) may have a HOMO level that is the same as or deeper (further from vacuum) than the LUMO level of the organic semiconductor, optionally at least 1 eV or 1.5 eV deeper. Accordingly, limited or no spontaneous n-doping may occur upon mixing of the compound of formula (I) with such an organic semiconductor at 20° C.

The n-dopant radical formed by cleavage of the C—H bond illustrated in formulae (I) preferably has a singly-occupied molecular orbital (SOMO) level that is shallower (closer to vacuum) than the LUMO level of the organic semiconductor acceptor material. Preferably, the n-dopant has a SOMO level that is at least 0.1 eV shallower than the LUMO level of the material comprising a repeat unit of formula (I), optionally at least 0.5 eV.

n-doping may occur upon activation of the compound of formula (I) and/or the organic semiconductor.

A film comprising the organic semiconductor and the compound of formula (I) may be formed prior to activation. Optionally, the film is formed in air.

Exemplary activation methods are thermal treatment and irradiation.

Optionally, thermal treatment is at a temperature in the range 80° C. to 170° C., preferably 100° C. to 150° C.

Thermal treatment and irradiation as described herein may be used together.

For irradiation, any wavelength of light may be used, for example a wavelength having a peak in the range of about 200-700 nm.

The light emitted from the light source suitably overlaps with an absorption feature, for example an absorption peak or shoulder, of the absorption spectrum of the organic semiconductor. Optionally, the light emitted from the light source has a peak wavelength within 25 nm, 10 nm or 5 nm of an absorption maximum wavelength of the organic semiconductor, however it will be appreciated that a peak wavelength of the light need not coincide with an absorption maximum wavelength of the organic semiconductor. Optionally, irradiation time is between 1 second and 1 hour, optionally between 1-30 minutes.

In one embodiment, the light emitted from the light source used for irradiation is in the range 400-700 nm. Optionally, the electromagnetic radiation has a peak wavelength greater than 400 nm, optionally greater than 420 nm, optionally greater than 450 nm Optionally, there is no overlap between an absorption peak in the absorption spectrum of the compound of formula (I) and the wavelength(s) of light emitted from the light source.

In another embodiment, the light-emitted from the light source used for irradiation has a peak wavelength of 400 nm or less.

Optionally, the electromagnetic radiation source is an array of inorganic LEDs. The electromagnetic radiation source may produce radiation having one or more than one peak wavelengths.

Preferably, the electromagnetic radiation source has a light output of at least 2000 mW, optionally at least 3000 mW, optionally at least 4000 mW.

Any suitable electromagnetic radiation source may be used to irradiate the film including, without limitation, fluorescent tube, incandescent bulb and organic or inorganic LEDs.

The extent of doping may be controlled by one or more of: the organic semiconductor material/compound of formula (I) ratio; the temperature and duration of heating if activation comprises heating; and the peak wavelength and intensity of the light and the duration of irradiation of the film if activation comprises irradiation.

The n-doped material may be an extrinsic or degenerate semiconductor.

Organic Light-Emitting Device

Figure 1:
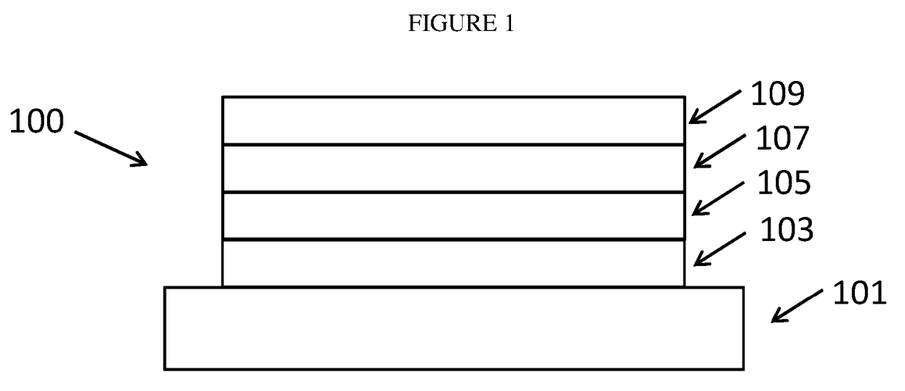
FIG. 1 illustrates schematically an OLED according to an embodiment of the invention.

FIG. 1, which is not drawn to any scale, illustrates an OLED 100 according to an embodiment of the invention supported on a substrate 101, for example a glass or plastic substrate. The OLED 100 comprises an anode 103, a light-emitting layer 105, an electron-injecting layer 107 and a cathode 109.

The anode 103 may be single layer of conductive material or may be formed from two or more conductive layers. Anode 103 may be a transparent anode, for example a layer of indium-tin oxide. A transparent anode 103 and a transparent substrate 101 may be used such that light is emitted through the substrate. The anode may be opaque, in which case the substrate 101 may be opaque or transparent, and light may be emitted through a transparent cathode 109.

Light-emitting layer 105 contains at least one light-emitting material. Light-emitting material 105 may consist of a single light-emitting material or may be a mixture of more than one material, optionally a host doped with one or more light-emitting dopants.

Light-emitting materials of the OLED 100 may be fluorescent materials, phosphorescent materials or a mixture of fluorescent and phosphorescent materials. Light-emitting materials may be selected from polymeric and non-polymeric light-emitting materials. Exemplary light-emitting polymers are conjugated polymers, for example polyphenylenes and polyfluorenes examples of which are described in Bernius, M. T., Inbasekaran, M., O'Brien, J. and Wu, W., Progress with Light-Emitting Polymers. Adv. Mater., 12 1737-1750, 2000, the contents of which are incorporated herein by reference. Light-emitting layer 105 may comprise a host material and a fluorescent or phosphorescent light-emitting dopant. Exemplary phosphorescent dopants are row 2 or row 3 transition metal complexes, for example complexes of ruthenium, rhodium, palladium, rhenium, osmium, iridium, platinum or gold.

Light-emitting layer 105 may be formed by any suitable method including, without limitation, thermal evaporation and solution deposition. Preferably, light-emitting layer 105 is formed by depositing a solution in which the solvent is one or more non-polar solvent materials, optionally benzenes substituted with one or more substituents selected from $C_{1-10}$ alkyl and $C_{1-10}$ alkoxy groups, for example toluene, xylenes and methylanisoles, and mixtures thereof.

Electron-injecting layer 107 comprises or consists of a charge-transfer complex formed from a compound of formula (I) and an organic semiconductor. The electron-injecting layer may comprise or consist of the charge-transfer salt. In addition to the charge-transfer complex, electron-injection layer 107 may comprise undoped organic semiconductor and/or a compound of formula (I).

Cathode 109 is formed of at least one layer, optionally two or more layers, for injection of electrons into the device.

Preferably, the electron-injecting layer 107 is adjacent to organic light-emitting layer 105.

Preferably, the organic semiconductor has a LUMO that is no more than about 1 eV, optionally less than 0.5 eV or 0.2 eV, deeper (i.e. further from vacuum) than a LUMO of a material of the light-emitting layer, which may be a LUMO of a light-emitting material or a LUMO of a host material if the light-emitting layer comprises a mixture of a host material and a light-emitting material. Optionally, the doped material has a work function that is about the same as a LUMO of a material of the light-emitting layer. Optionally, the material comprising a repeat unit of formula (I) has a LUMO of less (i.e. closer to vacuum) than 3.2 or 3.0 eV from vacuum level, optionally around 2.1 to 2.8 eV from vacuum level.

Preferably, the cathode 109 is in contact with the electron-injecting layer 107.

The cathode may comprise one or more layers. Preferably, the cathode comprises or consists of a layer in contact with the electron injecting layer that comprises or consists of one or more conductive materials. Exemplary conductive materials are metals, preferably metals having a work function of at least 4 eV, optionally aluminium, copper, silver, gold or iron. Exemplary non-metallic conductive materials include conductive metal oxides, for example indium tin oxide and indium zinc oxide, graphite and graphene. Work functions of metals are as given in the CRC Handbook of Chemistry and Physics, 12-114, 87th Edition, published by CRC Press, edited by David R. Lide. If more than one value is given for a metal then the first listed value applies.

The cathode may be opaque or transparent. Transparent cathodes are particularly advantageous for active matrix devices because emission through a transparent anode in such devices is at least partially blocked by drive circuitry located underneath the emissive pixels.

It will be appreciated that a transparent cathode device need not have a transparent anode (unless a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

The OLED 100 may be a display, optionally a full-colour display wherein the light-emitting layer 105 comprises pixels comprising red, green and blue subpixels.

The OLED 100 may be a white-emitting OLED. White-emitting OLEDs as described herein may have a CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K. A white-emitting OLED may contain a plurality of light-emitting materials, preferably red, green and blue light-emitting materials, more preferably red, green and blue phosphorescent light-emitting materials, that combine to produce white light. The light-emitting materials may all be provided in light-emitting layer 105, or one or more additional light-emitting layers may be provided.

A red light-emitting material may have a photoluminescence spectrum with a peak in the range of about more than 550 up to about 700 nm, optionally in the range of about more than 560 nm or more than 580 nm up to about 630 nm or 650 nm.

A green light-emitting material may have a photoluminescence spectrum with a peak in the range of about more than 490 nm up to about 560 nm, optionally from about 500 nm, 510 nm or 520 nm up to about 560 nm.

A blue light-emitting material may have a photoluminescence spectrum with a peak in the range of up to about 490 nm, optionally about 450-490 nm.

Photoluminescence spectra described herein are as measured by casting 5 wt % of the material in a polystyrene film onto a quartz substrate and measuring in a nitrogen environment using apparatus C9920-02 supplied by Hamamatsu.

Light-emitting layer 105 may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

The OLED 100 may contain one or more further layers between the anode 103 and the cathode 109, for example one or more charge-transporting, charge-blocking or charge-injecting layers. Preferably, the device comprises a hole-injection layer comprising a conducting material between the anode and the light emitting layer 105. Preferably, the device comprises a hole-transporting layer comprising a semiconducting hole-transporting material between the anode 103 and the light emitting layer 105.

A hole transporting layer provided between the anode 103 and the light-emitting layer 105 may be cross-linked, particularly if an overlying layer is deposited from a solution.

A hole transporting layer may comprise or may consist of a hole-transporting polymer, which may be a homopolymer or copolymer comprising two or more different repeat units. The hole-transporting polymer may be conjugated or non-conjugated. Exemplary conjugated hole-transporting polymers are polymers comprising arylamine repeat units, for example as described in WO 99/54385 or WO 2005/049546 the contents of which are incorporated herein by reference. Conjugated hole-transporting copolymers comprising arylamine repeat units may have one or more co-repeat units selected from arylene repeat units, for example one or more repeat units selected from fluorene, phenylene, phenanthrene naphthalene and anthracene repeat units, each of which may independently be unsubstituted or substituted with one or more substituents, optionally one or more $C_{1-40}$ hydrocarbyl substituents.

If present, a hole transporting layer located between the anode and the light-emitting layer 105 preferably has a HOMO level of less than or equal to 5.5 eV, more preferably around 4.8-5.5 eV or 5.1-5.3 eV as measured by cyclic voltammetry. The HOMO level of the hole transport layer may be selected so as to be within 0.2 eV, optionally within 0.1 eV, of an adjacent layer in order to provide a small barrier to hole transport between these layers.

Preferably a hole-transporting layer, more preferably a crosslinked hole-transporting layer, is adjacent to the light-emitting layer 105.

A hole-transporting layer may consist essentially of a hole-transporting material or may comprise one or more further materials. A light-emitting material, optionally a phosphorescent material, may be provided in the hole-transporting layer.

A phosphorescent material may be covalently bound to a hole-transporting polymer as a repeat unit in the polymer backbone, as an end-group of the polymer, or as a side-chain of the polymer. If the phosphorescent material is provided in a side-chain then it may be directly bound to a repeat unit in the backbone of the polymer or it may be spaced apart from the polymer backbone by a spacer group. Exemplary spacer groups include $C_{1-20}$ alkyl and aryl-$C_{1-20}$ alkyl, for example phenyl-$C_{1-20}$ alkyl. One or more carbon atoms of an alkyl group of a spacer group may be replaced with O, S, C=O or COO.

Emission from a light-emitting hole-transporting layer and emission from light-emitting layer 105 may combine to produce white light.

A conductive hole injection layer, which may be formed from a conductive organic or inorganic material, may be provided between the anode 103 and the light-emitting layer 105 of an OLED as illustrated in FIG. 1 to assist hole injection from the anode into the layer or layers of semiconducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted poly-thiophene or poly(thienothiophene). Examples of conductive inorganic materials include transition metal oxides such as VOx MoOx and RuOx as disclosed in Journal of Physics D: Applied Physics (1996), 29(11), 2750-2753.

Film Formation

An n-doped film, for example an electron-injection layer, may be formed by depositing a film of the organic semiconductor and the compound of formula (I) followed by activation.

The organic semiconductor and the compound of formula (I) may be deposited by any suitable method including, without limitation, thermal evaporation and from a solution.

Preferably, the film is deposited from a solution in a solvent, preferably a polar solvent.

The solvent or solvent mixture may be selected to prevent dissolution of the underlying layer, for example a light-emitting layer of an OLED.

Preferably, the electron-injecting layer is formed from a solution in a polar solvent. Preferably, the electron-injecting layer is formed on a layer (preferably a light-emitting layer) formed from a solution in a non-polar solvent.

"Solvent" as used herein includes a single solvent material or a mixture of two or more solvent materials. A non-polar solvent may consist of a single non-polar solvent material or a plurality of non-polar solvent materials. A polar solvent may consist of a single polar solvent material or a plurality of polar solvent materials.

Non polar solvents are preferably aprotic. Exemplary non-polar solvents are chloroform, benzenes substituted with one or more substituents selected from $C_{1-10}$ alkyl and $C_{1-10}$ alkoxy groups, for example toluene, xylenes and methylanisoles, and mixtures thereof. Non polar aprotic solvents are preferably aprotic solvents having a dielectric constant at 20° C. of less than 8.

Polar solvents may be protic or aprotic. Exemplary protic solvents are water and alcohols, for example methanol, ethanol, propanol, butoxyethanol, ethylene glycol, 1-methoxy-2-propanol and monofluoro-, polyfluoro- or perfluoro-alcohols, optionally 2,2,3,3,4,4,5,5-octafluoro-1-pentanol. Exemplary aprotic polar solvents are dimethylsulfoxide; propylene carbonate; and 2-butanone. Aprotic polar solvents preferably have a dielectric constant at 20° C. of at least 15 or at least 20.

Particularly preferred solution deposition techniques including printing and coating techniques such spin-coating, inkjet printing and lithographic printing.

Coating methods are particularly suitable for devices wherein patterning of the light-emitting layer is unnecessary—for example for lighting applications or simple monochrome segmented displays.

Printing methods are particularly suitable for high information content displays, in particular full colour displays. A device may be inkjet printed by providing a patterned layer over the anode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, slot die coating, roll printing and screen printing.

Encapsulation

The n-dopant is preferably activated to cause n-doping as described herein after encapsulation of a device containing the n-doped film to prevent ingress of moisture and oxygen.

Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

The substrate on which the device is formed preferably has good barrier properties such that the substrate together with the encapsulant form a barrier against ingress of moisture or oxygen. The substrate may be glass. The substrate may comprise one or more plastic layers, for example a substrate of alternating plastic and dielectric barrier layers or a flexible laminate of thin glass and plastic.

Applications

An n-doped layer formed from a compound of formula (I) and an organic semiconductor has been described for use as the electron-injection layer of an organic light-emitting device formed over an organic light-emitting layer, however it will be appreciated that the layer formed as described herein may be used in other organic electronic devices, for example as an electron-extraction layer of an organic photovoltaic device or organic photodetector; as an auxiliary electrode layer of a n-type organic thin film transistor or as an n-type semiconductor in a thermoelectric generator.

Measurements

UV-visible absorption spectra of pristine and n-doped acceptor materials as described herein were measured by spin-coating onto glass substrates, as blend with the dopant. The film thicknesses were in the range of 20-100 nm.

After spin-coating and drying, the polymer films were encapsulated in a glove box, in order to exclude any contact of the n-doped films with air.

After the encapsulation, UV-vis absorption measurements were conducted with a Carey-5000 Spectrometer, followed by successive exposures to visible light and repeat UV-VIS measurements.

HOMO, SOMO and LUMO levels as described anywhere herein are as measured by square wave voltammetry.

Equipment:
CHI660D Electrochemical workstation with software (IJ Cambria Scientific Ltd))
CHI 104 3 mm Glassy Carbon Disk Working Electrode (IJ Cambria Scientific Ltd))
Platinum wire auxiliary electrode
Reference Electrode (Ag/AgCl) (Havard Apparatus Ltd)
Chemicals

| | |
|---|---|
| Acetonitrile (Hi-dry anhydrous grade-ROMIL) | (Cell solution solvent) |
| Toluene (Hi-dry anhydrous grade) | (Sample preparation solvent) |
| Ferrocene - (FLUKA) | (Reference standard) |
| Tetrabutylammonium-hexafluorophosphate (FLUKA) | (Cell solution salt) |

Sample Preparation

The acceptor polymers were spun as thin films (~20 nm) onto the working electrode; the dopant material was measured as a dilute solution (0.3 w %) in toluene.

Electrochemical Cell

The measurement cell contains the electrolyte, a glassy carbon working electrode onto which the sample is coated as a thin film, a platinum counter electrode, and a Ag/AgCl reference glass electrode. Ferrocene is added into the cell at the end of the experiment as reference material (LUMO (ferrocene)=−4.8 eV).

EXAMPLES

Compound Example 1

Synthesis of 2,2'-Iminodibenzoic acid

An oven dried 4000 ml four neck flask fitted with nitrogen inlet, condenser and overhead stirrer was charged with 2-bromobenzoic acid (50.0 g, 248.73 mmol), anthranilic acid (34.11 g, 248.73 mmol) and anhydrous potassium carbonate (77.35 g, 559.65 mmol). Air was replaced with nitrogen for 30 min Anhydrous DMF (300 ml) was added and stirred. Copper powder (1.58 g, 24.87 mmol) was added followed by $Cu_2O$ (1.78 g, 12.44 mmol). The reaction mixture was heated to 130° C. for 20 hrs. The reaction was stopped and cooled down to room temperature. Most of the DMF was evaporated off under reduced pressure. Water (500 ml) was added to the residue and stirred. The reaction mixture was acidified with aqueous HCl to pH=4 which resulted in a grey precipitate. It was filtered and washed thoroughly with water (700 ml×3). LC-MS showed a mass for the desired product with a trace of unreacted anthranilic acid left. The grey solid was dried in an oven at 50° C. under vacuum (63 g, yield quantitative). The material was used for the next step without further purification.

$^1$H-NMR (600 MHz, THF-d8): δ=11.4 (brs, 1H), 10.92 (s, 1H), 7.97 (d, 2H), 7.49 (d, 2H), 7.33 (m, 2H), 6.85 (m, 2H).

Synthesis of 2,2'-iminodibenzoyl chloride

In an oven dried 1000 ml three neck flask fitted with condenser/scrubber solution, dropping funnel and overhead stirrer was charged with 2,2'-iminodibenzoic acid (25 g, 97.19 mmol). Thionyl chloride (57.81 g, 485.93 mmol) was added slowly with stirring. With addition of thionyl chloride slow evolution of gas was observed. The reaction mixture was stirred at room temperature for 30 min then 20 ml of toluene was added and heated the reaction mixture to 80° C. for 1.5 hr. The reaction was stopped, cooled down to room temperature and pentane (200 ml) was added with stirring. A bright yellow solid was precipitated out which was filtered and washed thoroughly with pentane (200 ml). The solid was collected and again suspended in pentane (300 ml) and stirred for 10 min then filtered and washed with pentane (100 ml). The product was dried overnight in an oven at 30° C. under vacuum. Bright yellow flakes were obtained (25.5 g, yield 89%, 100% pure by LC-MS).

$^1$H-NMR (600 MHz, CDCl3): δ=10.34 (s, 1H), 8.27 (d, 2H), 7.51 (m, 4H), 7.07 (m, 2H).

Synthesis of 1,1'-(2,2'-Iminodibenzoyl)bisbenzimidazole

In an oven dried 2000 ml four neck flask fitted with overhead stirrer, nitrogen inlet and dropping funnel 2,2'-iminodibenzoyl chloride (25.0 g, 85.0 mmol) was added. Air was replaced with nitrogen for 30 min Anhydrous THF (1 L) was added and stirred, a yellow colour clear was solution obtained. Benzimidazole (20.08 g, 169.99 mmol) was added into the reaction mixture portion wise during which pale yellow precipitation observed. Triethylamine (29.6 ml, 212.49 mmol) was added dropwise into the reaction mixture. The progress of reaction was followed by TLC and GC-MS analysis. After 3 hr no starting materials was left. The reaction was stopped and the precipitated trimethylamine salt was filtered and washed with THF (300 ml). The filtrate was collected and concentrated to about 200 ml to which heptane (600 ml) was added with stirring. A yellow precipitation was obtained. The precipitate was filtered and washed with heptane to give a yellow solid. The precipitation was repeated form THF/heptane giving pure material, 16.8 g, yield 43%, 99.59% HPLC.

$^1$H-NMR (600 MHz, CDCl3): δ=9.64 (s, 1H), 8.11 (d, 2H), 8.09 (s, 2H), 7.79 (m, 2H), 7.52 (m, 6H), 7.41 (m, 4H), 7.07 (m, 2H).

Synthesis of Triazadibenzo[a,e]acephenanthrylene-9,14-dione 1,1'-(2,2'-Iminodibenzoyl)bisbenzimidazole (7.0 g, 15.30 mmol) was taken in a Kugelrohr distillation apparatus then slowly heated to 180° C. and 5.7 mbar pressure during which the colour of the solid changes from yellow to pale yellow. After 4 hr the heating was stopped and the reaction mixture was cooled down to room temperature. The pale yellow solid was collected and purified by recrystallization from THF/heptane, 2.97 g, 57% yield, 99.06% HPLC.

$^1$H-NMR (600 MHz, CDCl3): δ=8.19 (d, 2H), 8.05 (m, 2H), 7.77 (d, 2H), 7.55 (m, 2H), 7.18 (m, 4H), 7.02 (s, 1H).

Synthesis of Compound Example 1,
Triazadibenzo[a,e]acephenanthrylene

An oven dried 500 ml four neck flask fitted with nitrogen inlet and dropping funnel was charged with anhydrous AlCl$_3$ (1.65 g, 12.38 mmol) under nitrogen. Dry THF (60 ml) was added and stirred, a clear solution obtained. The flask was cooled down to −40° C. using dry ice/acetone bath then LiAlH$_4$ (35 mmol, 1M solution in THF) was added dropwise. The mixture was stirred at −40° C. for 10 min then allowed to warm to 0° C. and stirred for additional 10 min.

A THF (150 ml) solution of triazadibenzo[a,e]acephenanthrylene-9,14-dione (2.5 g, 7.37 mmol) prepared separately under nitrogen was added dropwise to the above reaction mixture at 0° C. and it was then allowed to warm to room temperature overnight (16 hr). TLC shows that no starting material left and LC-MS analysis shows the mass of the desired product.

The reaction mixture was cooled down to 0° C. and quenched with 7.0 ml of 25% aqueous NaOH solution and then with water (7.0 ml). It was filtered thought a celite plug and washed with THF. The filtrate was concentrated to dryness. The crude product was purified by silica gel column chromatography using 30% ethyl acetate/heptane as eluent followed by recrystallisation from dichloromethane/pentane giving a white solid; 1.0 g, 54% yield.

$^1$H-NMR (600 MHz, CDCl3): δ=7.20 (d, 2H), 7.16 (d, 2H), 7.09 (m, 2H), 6.89 (m, 2H), 6.63 (m, 2H), 6.43 (m, 2H), 6.22 (s, 1H), 4.61 (d, 2H), 4.45 (d, 2H).

Compound Example 2

Compound Example 2 may be prepared according to the following reaction scheme:

Materials Data

The SOMO level of Compound Example 1 was measured by square wave voltammetry as described herein. As shown in Table 1, Compound Example 1 has a slightly shallower SOMO than comparative compound N-DMBI:

N-DMBI

TABLE 1

| Compound | SOMO/eV vs vacuum energy |
| --- | --- |
| Compound Example 1 | −2.50 |
| N-DMBI | −2.55 |

Solution Stability

Figure 2A:
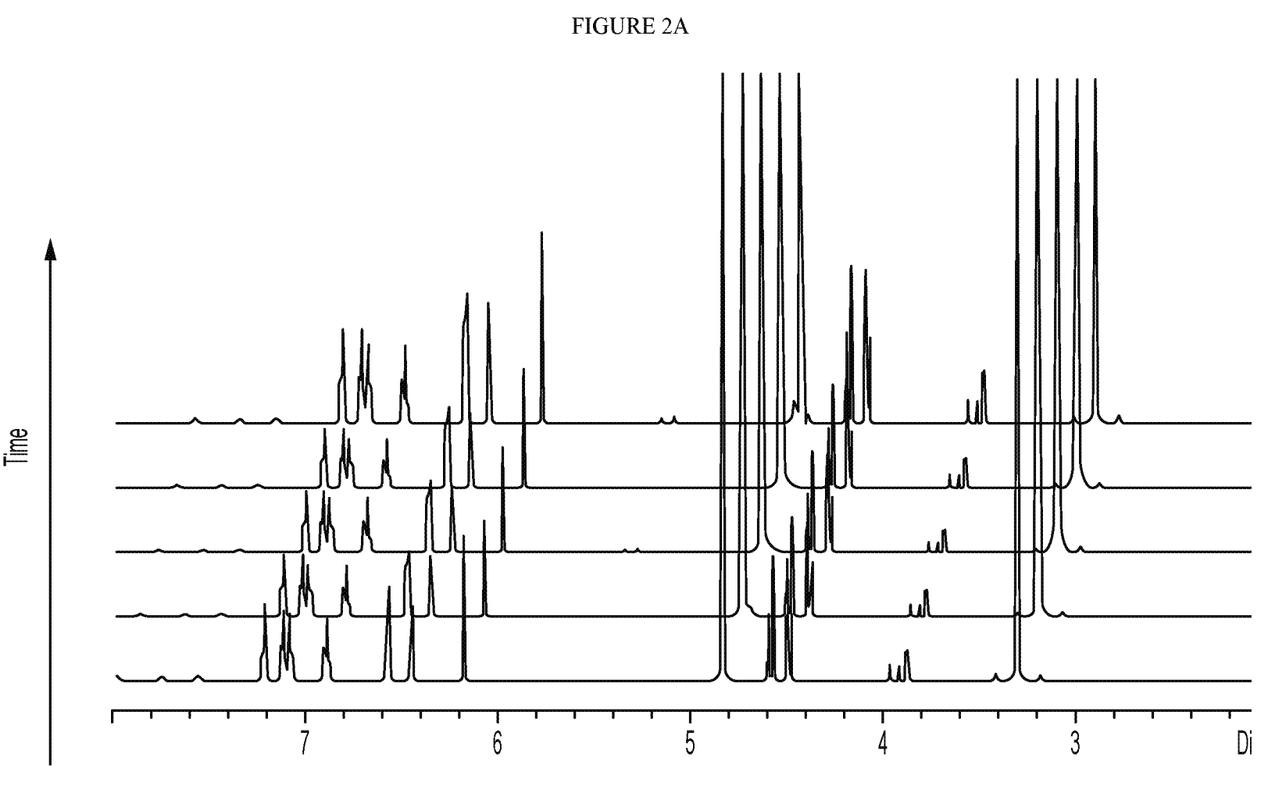
FIG. 2A shows changes in NMR spectra over time of a solution of a compound according to an embodiment of the invention in deuterated methanol.

Compound Example 1 was dissolved in deuterated methanol ($CD_3OD$) and its NMR spectrum was measured at 0 hr, 3.5 hr, 7 hr, 12 hr, 17 hr, 54 hr & 120 hr after sample preparation. With reference to FIG. 2A, there is little change in the spectra over time.

Figure 2B:
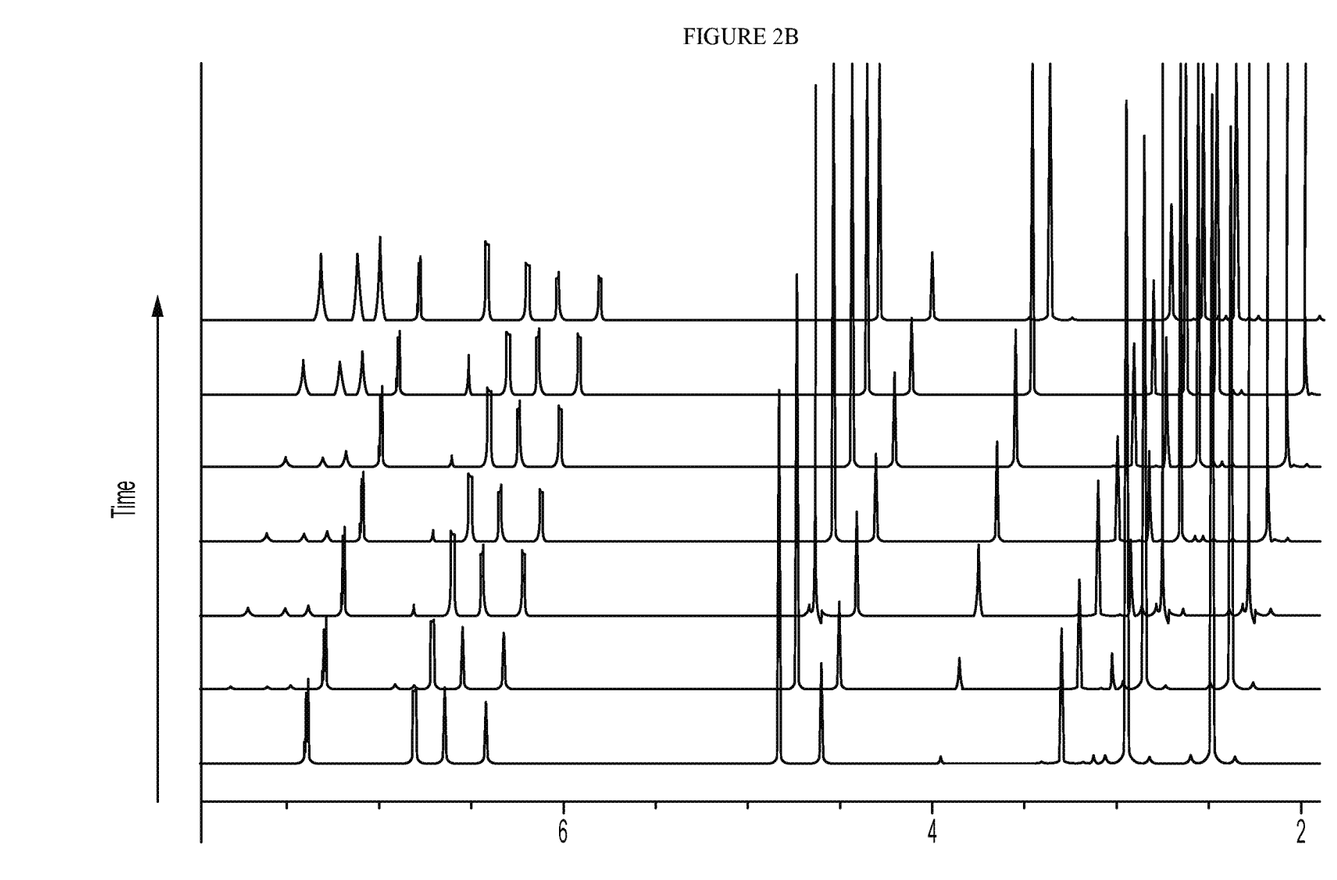
FIG. 2B shows changes in NMR spectra over time of a comparative compound in deuterated methanol

For comparison, the same measurements were made for a solution of N-DMBI, illustrated below. With reference to FIG. 2B, significant growth of peaks over time is observed.

Figure 3:
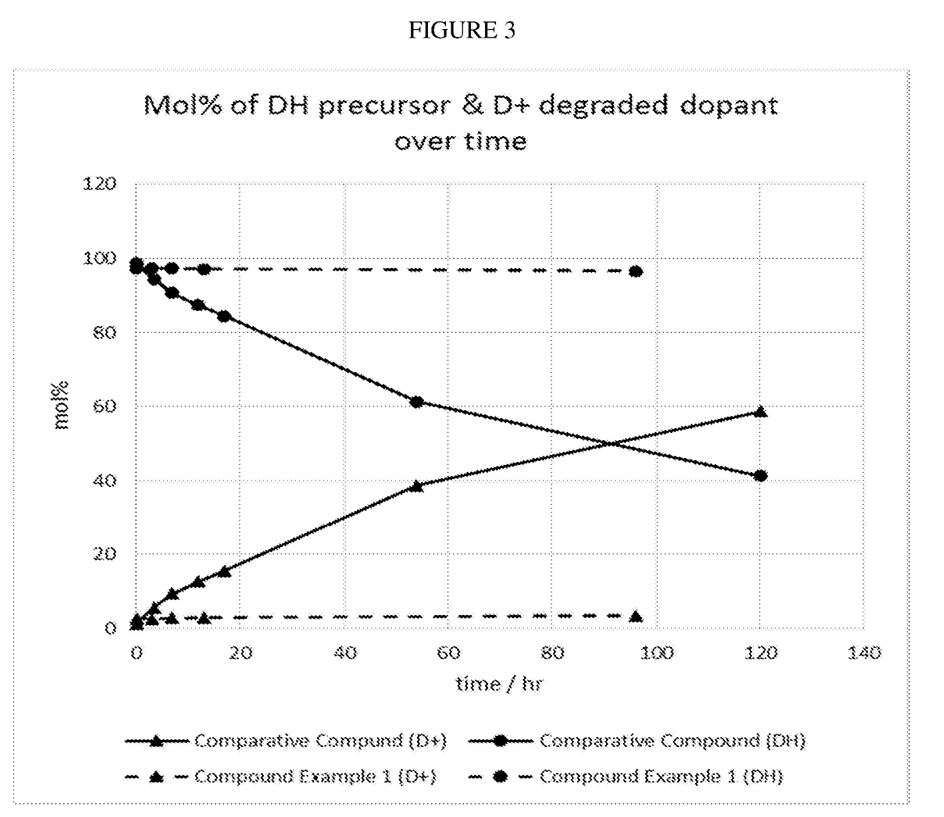
FIG. 3 shows a change in integrated NMR spectra of FIGS. 2A and 2B over time.

Without wishing to be bound by any theory, the degradation of N-DMBI is attributed to oxidation of this compound. FIG. 3 shows relative mole percentages calculated by integration of the NMR spectra of FIGS. 2A and 2B showing change over time of Compound Example 1 and comparative compound N-DMBI from their initial form (D-H) to $D^+$.

There is little or no change over time observed for Compound Example 1 whereas the comparative compound shows a decrease in the initial form D-H and a corresponding increase in $D^+$.

Film Example

A film of Acceptor Polymer 1 and Compound Example 1 (1:1 w/w) was deposited by spin-coating from methanol solution onto a glass substrate. The photoluminescence spectrum of the resulting film was measured. The film was then heated and the spectrum was measured again.

Acceptor Polymer 1 has the following structure:

Acceptor Polymer 1 was formed by Suzuki polymerization as disclosed in WO00/53656 of 50 mol % each of the following monomers to form a precursor polymer followed by hydrolysis of the precursor polymer:

To hydrolyse the polymer, nitrogen was bubbled separately for 30 minutes in 113 ml of tetrahydrofuran, in 42 ml of methanol and in a solution of cesium hydroxide (0.80 g, 4.73 mmol) in 3.4 ml of water. 2.24 g of the precursor polymer was suspended in the tetrahydrofuran and heated up to 65° C. Mixture was stirred until full dissolution of the polymer. Methanol was added drop wise followed by the cesium hydroxide solution. Mixture was stirred at 65° C. for 16 hours and cooled down to room temperature. Solution was filtered and concentrated to 42 ml. It was precipitated into 800 ml of diethyl ether. The slurry was stirred for 10 minutes and filtered. Polymer was dried in vacuum oven at 50° C. overnight to yield 2.52 g of Acceptor Polymer 1, 96% yield.

Figure 4:
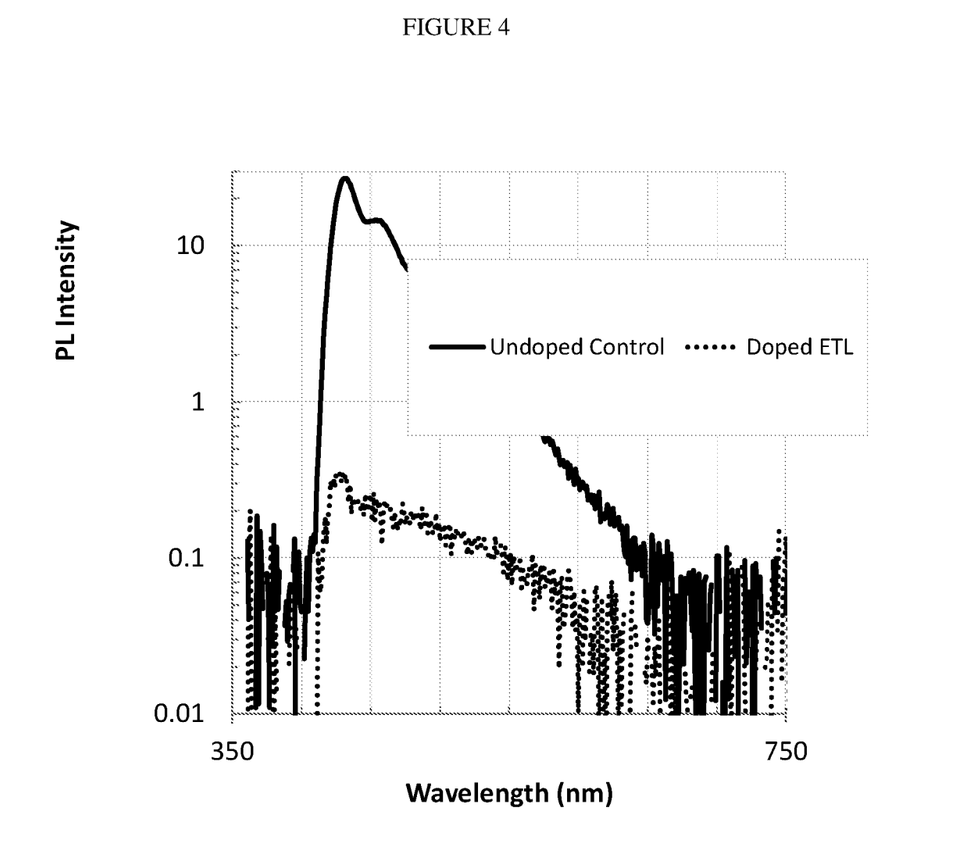

With reference to FIG. 4, the photoluminescence intensity of the film falls sharply after heating, indicating doping of the polymer upon heating.

Device Examples

A first device having the following structure was formed:
ITO/HIL (50 nm)/LEL (80 nm)/EIL/Ag (100 nm)
in which ITO is an indium tin oxide anode; HIL is a hole-injection layer; EIL is an electron injection layer and LEL is a light-emitting layer.

The electron injection layer was formed by spin-coating a composition of Acceptor Polymer 1 and Compound Example 1 (1:1 w/w) from methanol solution onto the light-emitting layer to form a 10 nm thick electron injection layer. The device was heated at 130° C. following deposition of the cathode.

A second device was formed as described above except that the electron injection layer was formed to a thickness of 50 nm.

The capacitance of the two devices was measured and was found to be the same, indicating that the Acceptor Polymer 1 is doped in the completed device resulting in the electron-injecting layer behaving as a conductor, in contrast to an (undoped) semiconductor giving higher device capacitance at higher layer thicknesses.

Although the present invention has been described in terms of specific exemplary embodiments, it will be appreciated that various modifications, alterations and/or combinations of features disclosed herein will be apparent to those skilled in the art without departing from the scope of the invention as set forth in the following claims

The invention claimed is:

1. A compound of formula (I):

wherein $Ar^1$, $Ar^2$ and $Ar^3$ independently in each occurrence is a $C_{6-20}$ aryl group or a 5-20 membered heteroaryl group which is unsubstituted or substituted with one or more substituents; $X^1$ is a direct bond, and $X^2$ and $X^3$ in each occurrence is a group of formula —$C(R^1)_2$— wherein $R^1$ in each occurrence is independently H or a substituent.

2. A compound according to claim 1 wherein $Ar^1$, $Ar^2$ and $Ar^3$ are each independently phenyl which may be unsubstituted or substituted with one or more substituents.

3. A compound according to claim 1 wherein at least one of $Ar^1$, $Ar^2$ and $Ar^3$ is substituted with at least one substituent $R^2$ wherein each $R^2$ is independently selected from ionic and non-ionic substituents.

4. A compound according to claim 3 wherein at least one substituent $R^2$ is a non-ionic substituent wherein the non-ionic substituent is a $C_{1-20}$ alkyl wherein one or more non-adjacent, non-terminal C atoms may be replaced with O, S, $NR^3$, $PR^3$, $Si(R^3)_2$, C=O, C(=O)O, C(=O)$NR^3$, OC(=O)O, $NR^3$C(=O)O, or $NR^3$C(=O)$NR^3$ and wherein one or more H atoms may be replaced with F, wherein $R^3$ independently in each occurrence is a $C_{1-20}$ hydrocarbyl group.

5. A compound according to claim 3 wherein at least one substituent $R^2$ is an ionic substituent.

6. A compound according to claim 5 wherein the or each ionic substituent is a group of formula (III):

$$-(Sp^1)p-(A)q \qquad (III)$$

wherein $Sp^1$ is a spacer group; A is an anion or cation; p is 0 or 1; q is 1 if p is 0; and q is an integer of at least 1 if p is 1, the compound further comprising one or more counterions B to balance the charge of the one or more anions or cations A.

7. A compound according to claim 6 wherein the or each B is an alkali metal cation.

8. A compound according to claim 3 wherein only one of $Ar^1$, $Ar^2$ and $Ar^3$ is substituted.

9. A compound according to claim 8 wherein the substituted group $Ar^1$, $Ar^2$ or $Ar^3$ is substituted with only one substituent.

10. A compound according to claim 1 wherein each of $Ar^1$, $Ar^2$ and $Ar^3$ is unsubstituted.

11. A composition comprising an organic semiconductor and a compound according to claim 1.

12. A formulation comprising a compound according to claim 1 and at least one solvent.

13. A formulation according to claim 12 wherein the solvent comprises at least one polar solvent material.

14. A charge-transfer salt comprising an organic semiconductor doped by a dopant formed from a compound according to claim 1.

15. An organic electronic device comprising a layer comprising a charge-transfer salt according to claim 14.

16. An organic electronic device according to claim 15 wherein the organic electronic device is an organic light-emitting device comprising an anode, a cathode and a light-emitting layer between the anode and the cathode and wherein the layer comprising the charge-transfer salt is an electron injection layer between the light-emitting layer and the cathode.

17. An organic electronic device according to claim 16 wherein the electron injection layer is in contact with the light-emitting layer.

18. A method of forming an organic electronic device according to claim 15 comprising the step of depositing the compound from a polar solvent.

\* \* \* \* \*